US005352975A

United States Patent [19]

Ueno

[11] Patent Number: 5,352,975
[45] Date of Patent: Oct. 4, 1994

[54] CORPUSCLE-DETECTING APPARATUS HAVING SENSITIVITY ADJUSTMENT

[75] Inventor: Kunio Ueno, Kakogawa, Japan

[73] Assignee: Toa Medical Electronics Co., Ltd., Kobe, Japan

[21] Appl. No.: 15,385

[22] Filed: Feb. 9, 1993

[30] Foreign Application Priority Data

Mar. 4, 1992 [JP] Japan .................. 4-047139

[51] Int. Cl.$^5$ .......................................... G01N 27/02
[52] U.S. Cl. ................................... 324/71.4; 324/710; 377/12
[58] Field of Search .................. 324/71.4, 692, 710; 377/12; 128/734

[56] References Cited

U.S. PATENT DOCUMENTS

| | | | |
|---|---|---|---|
| 3,316,896 | 5/1967 | Thomasset | 324/71.4 X |
| 3,691,381 | 9/1972 | Kleppner | 324/71.4 X |
| 3,745,455 | 7/1973 | Haigh | 324/71.1 |
| 3,970,928 | 7/1976 | Kachel | 324/71.1 |
| 4,218,610 | 8/1980 | Baxter, Jr. et al. | 377/12 |
| 4,804,909 | 2/1989 | Fink | 324/71.4 |

Primary Examiner—Kenneth A. Wieder
Assistant Examiner—Glenn W. Brown
Attorney, Agent, or Firm—Stevens, Davis, Miller & Mosher

[57] ABSTRACT

An apparatus for detecting corpuscles such as blood cells. The apparatus has an aperture and a constant-current source that supplies an electrical current to the aperture for detection of corpuscles. When corpuscles to be investigated pass through the aperture, the electrical impedance changes, producing a signal (herein referred to as the corpuscle signal). The apparatus further includes a pseudo signal-generating means for producing a pseudo signal in the form of pulses. The pseudo signal has a peak value proportional to the amplitude of the input current and is equivalent to the corpuscle signal detected when the corpuscles pass through the aperture. A signal selector means is disposed among the aperture, the constant-current source, and the pseudo signal-generating means. The signal selector means assumes either a first state or a second state. In the first state, the current from the power supply is supplied to the pseudo signal-generating means, and the pseudo signal produced by the pseudo signal-generating means is supplied to the aperture. In the second state, the current from the power supply is supplied to the aperture.

8 Claims, 10 Drawing Sheets

CORPUSCLE-DETECTING APPARATUS HAVING SENSITIVITY ADJUSTMENT

FIELD OF THE INVENTION

The present invention relates to a corpuscle-detecting apparatus which passes a liquid sample containing blood cells or other corpuscles to be investigated through an aperture in a detector portion and detects the resulting change in the electrical impedance to thereby count the number of the corpuscles and, more particularly, to a corpuscle-detecting apparatus which adjusts the sensitivity and which checks the operation thereof, using a pseudo signal.

BACKGROUND OF THE INVENTION

A known corpuscle-detecting apparatus passes a liquid sample containing blood cells or other corpuscles through an aperture in a detector portion and detects individual corpuscles, based on the difference in electrical impedance between the liquid and each corpuscle.

Figure 12:
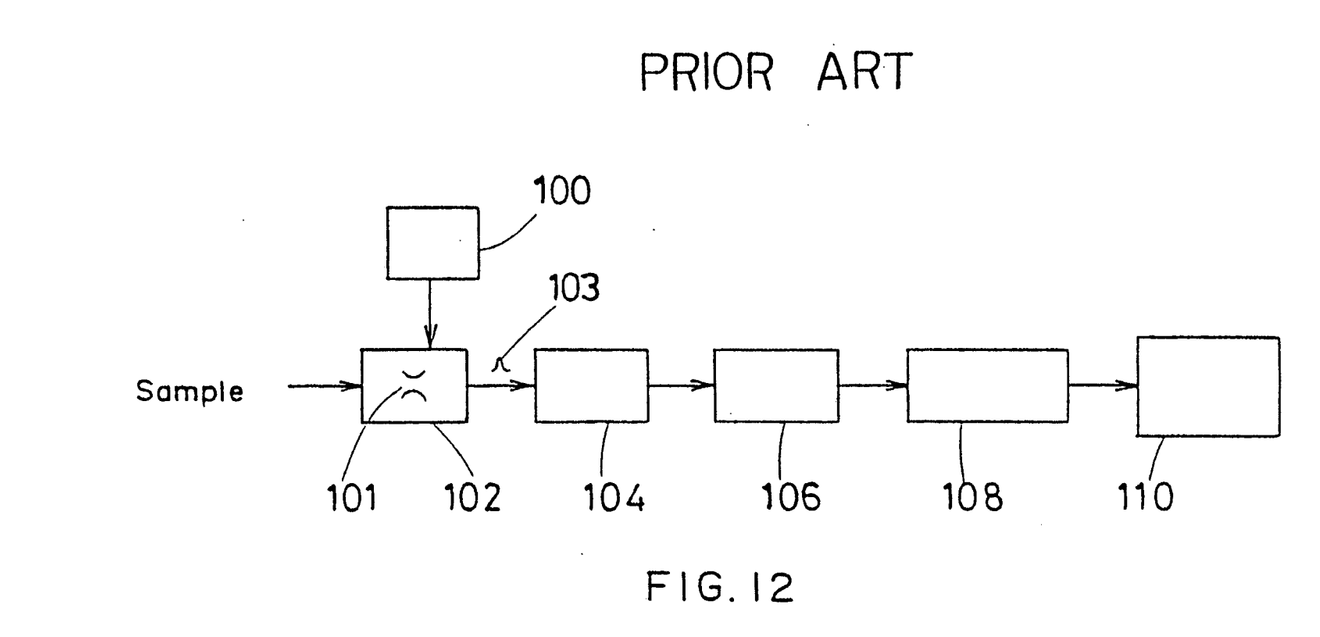
FIG. 12 is a block diagram of the prior art corpuscle-detecting apparatus.

FIG. 12 is a block diagram of such a corpuscle-detecting apparatus. This apparatus comprises a detector portion 102 having an aperture 101. A power supply 100 supplies a constant current to the aperture 101. Individual corpuscles are detected by the detector portion 102. The output signal 103 from this detector portion 102 is sent to an amplifier circuit 104, a waveform-processing circuit 106, an A/D converter circuit 108, and a data-processing circuit 110 which are disposed behind the detector portion 102. The signal is processed in these circuits in given manner, and the number and the sizes of the corpuscles are detected.

The corpuscle-detecting apparatus is required to adjust the sensitivity thereof and to check or monitor the operation of the circuits. Such adjustment and checking or monitoring has been done by the prior art techniques in the manner described below.

(1) Adjustment of Sensitivity

A control blood sample containing control corpuscles whose size are known and which are used for adjustment of the sensitivity is prepared. This control blood sample is actually supplied as a liquid sample into the detector portion 102. The gain of the amplifier circuit 104 is adjusted in such a manner that the counted value indicating the size of the corpuscles assumes a desired value.

(2) Check of the Operation of the Circuits

Each circuit to be checked is isolated from the other circuits. A pseudo signal used for checking purposes is applied to the checked circuit. The output from this circuit is investigated. In this manner, the operation of each circuit is checked.

(3) Check for Clogging

The DC component of the voltage developed between a pair of electrodes disposed on opposite sides of the aperture 101 is extracted. If this DC voltage exceeds a predetermined reference value, then the aperture is judged to be clogged. This is based on the fact that the obtained DC voltage value is associated with the diameter of the aperture 101. If the DC voltage value is affected by the temperature of the liquid sample, the value is corrected according to the temperature. The details are disclosed in Japanese Utility Model Laid-Open No. 85353/1990.

These prior art techniques have the following problems.

(1) The sensitivity is adjusted, using the control corpuscles, by trial and error. That is, a signal corresponding to the control corpuscles is measured. Then, the gain of the amplifier circuit is adjusted according to the signal. Again, a signal corresponding to the control corpuscles is measured. Hence, it is costly and time-consuming to adjust the sensitivity.

(2) Although the operation of each circuit such as the amplifier circuit 104 has been possible, it has been impossible to check the whole apparatus including the detector portion 102.

(3) Detection of clogging is possible only during measurement of corpuscles.

SUMMARY OF THE INVENTION

It is an object of the present invention to provide a corpuscle-detecting apparatus which can adjust the sensitivity without using control corpuscles to reduce the cost of the adjustment of the sensitivity and to shorten the time required for the adjustment of the sensitivity.

It is another object of the invention to provide a corpuscle-detecting apparatus capable of checking the operation of the whole circuit.

It is a further object of the invention to provide a corpuscle-detecting apparatus which can detect clogging even when corpuscles are not being detected.

A corpuscle-detecting apparatus according to the invention comprises a detector portion having an aperture, a power supply for supplying an electrical current to the aperture to detect the corpuscles, and a corpuscle signal-processing means. The detector portion has the aperture through which corpuscles to be investigated pass. The detector portion produces an output signal (herein referred to as the corpuscle signal) indicating corpuscles, based on a change in the electrical impedance caused by the passage of the corpuscles to be investigated. The corpuscle signal-processing means processes the corpuscle signal from the detector portion.

Also, a pseudo signal-generating means that produces a pseudo signal in the form of pulses is provided. The peak value of this pseudo signal corresponds to the amplitude of the input current and is equivalent to the output signal from the detector portion which is produced when corpuscles to be investigated pass through the aperture. A signal selector means is disposed between the pseudo signal-generating means and the body of the corpuscle-detecting apparatus comprising the aperture, the power supply, and the corpuscle signal-processing means.

The signal selector means is switched between a first state and a second state. In the first state, the current from the power supply used for detection of corpuscles is supplied to the pseudo signal-generating means, and the pseudo signal generated by the pseudo signal-generating means is supplied to the aperture. In the second state, the current from the power supply used for detection of corpuscles is supplied to the aperture.

The signal selector means can take the form of first and second switching means which are connected with the input and the output, respectively, of the pseudo signal-generating means.

When the signal selector means assumes its first state, the first switching means disconnects the power supply from an electrode on one side of the aperture and connects the power supply with the input of the pseudo signal-generating means. The second switching means connects the output of the pseudo signal-generating means with the electrode on the side of the aperture. When the signal selector means assumes its second state, the first switching means disconnects the power supply from the input of the pseudo signal-generating means and connects the power supply with the electrode on the side of the aperture. The second switching means disconnects the output of the pseudo signal-generating means with the electrode on the side of the aperture.

The signal selector means can also take the form of a switching means connected with the input of the pseudo signal-generating means. The output of the pseudo signal-generating means is directly connected with the electrode on the side of the aperture.

In this case, in the first state of the signal selector means, the switching means disconnects the power supply from the electrode on the side of the aperture and connects the power supply with the input of the pseudo signal-generating means. In the second state of the signal selector means, the switching means disconnects the power supply from the input of the pseudo signal-generating means and connects the power supply with the electrode on the side of the aperture.

One example of the pseudo signal-generating means comprises a control means which externally controls the timing at which the pseudo signal is produced.

A more specific example of the pseudo signal-generating means comprises a resistor for converting the current supplied from the power supply used for detection of corpuscles into a voltage and a pulse signal-generating means which produces pulses having a peak value corresponding to the voltage developed across the resistor at regular intervals of time. These pulse signals produced at regular intervals of time are delivered as a pseudo signal.

The pulse signal-generating means forming the pseudo signal-generating means can comprise an analog switch having one end to which the voltage produced across the aforementioned resistor is applied, an oscillator producing pulses at regular intervals of time for controlling the analog switch, and a pulse signal supply means for supplying these pulses to the control terminal of the analog switch for a desired period. Pulses having a peak value proportional to the voltage produced across the resistor are delivered from the other end of the analog switch.

The operation of the novel corpuscle-detecting apparatus is described now. When the signal selector means takes its first state, the power supply is connected with the pseudo signal-generating means. The pseudo signal-generating means produces a pseudo signal, which is supplied to the aperture. In this state, various adjustments, checks, and monitoring operations are performed. This state is hereinafter also referred to as the pseudo signal mode.

When the signal selector mode takes its second state, the power supply is disconnected from the pseudo signal-generating means. The current from the power supply is supplied to the aperture. This state is hereinafter also referred to as the normal measurement mode, i.e., the corpuscle-detecting apparatus performs normal measurements of corpuscles.

In the first state or in the pseudo signal mode, current used for detection of corpuscles is supplied from the power supply of the body of the apparatus to the pseudo signal-generating means. The pseudo signal-generating means detects the value of the supplied current for detection of corpuscles and produces a pseudo signal in the form of pulses. The peak value of the pseudo signal corresponds to the amplitude of the current for detection of the corpuscles. More specifically, the peak value is in proportion to the amplitude.

The pseudo signal is supplied to the aperture from the electrode. A pseudo corpuscle signal is produced according to the circumstances of the detector portion such as the diameter of the aperture. The signal is amplified, wave-shaped, or otherwise processed by the following stage forming a corpuscle signal-processing means.

The sensitivity is adjusted by varying the gain of the amplifier circuit forming the corpuscle signal-processing means in such a way that the peak value of the pseudo corpuscle signal caused by the pseudo signal assumes a given value.

The operation or clogging can be checked by monitoring signals processed by the various circuits, the signals arising from the pseudo signal.

In the second state of the signal selector means or in the normal measurement mode, the current used for detection of corpuscles is supplied to the side of the aperture from the power supply. Normal measurements of corpuscles are made. Prior to the measurements, the selector means is made to assume the first state. A pseudo signal is produced, and the sensitivity is inspected. In this way, clogging of the detector can be detected in advance.

The operation of the corpuscle signal-processing means at the following stage can be inspected with greater accuracy by designing the apparatus such that it can modify the waveform or the amplitude of the pseudo signal. These operations can be performed at any desired time, either prior to or after the measurements. The adjustments of the sensitivity, the check of the operation, and the check for clogging can be performed in this way.

The novel corpuscle-detecting apparatus comprises the pseudo signal-generating means and the signal selector means and, therefore, the apparatus can establish the pseudo signal mode in which the pseudo signal is supplied to the aperture and the normal measurement mode in which the apparatus performs normal detection of corpuscles without supplying the pseudo signal. Thus, in the normal measurement mode, normal measurements of corpuscles can be made. In the pseudo signal mode, the sensitivity can be adjusted without using control corpuscles or any special device. Hence, the cost of the sensitivity adjustment can be reduced. Also, the time required for the sensitivity adjustment can be shortened.

Furthermore, the operation of the whole circuit can be checked. Specifically, in the pseudo signal mode, the power supply for supplying the current used for detection of corpuscles and the aperture are contained in the apparatus. Consequently, the whole apparatus can be checked rather than just a part of the measuring system can be performed.

In the pseudo signal mode, the current used for detection of corpuscles in the normal measurement mode is applied to the pseudo signal-generating means. A pseudo signal having a peak value corresponding to the amplitude of the current used for the detection of corpuscles is produced and supplied to the aperture. Hence, each individual corpuscle-detecting apparatus of this construction can adjust its sensitivity irrespective of the detected current values the time constant, or gain of the amplifier of the circuit.

In addition, the mode of operation can be switched between the pseudo signal mode and the normal measurement mode quickly and easily according to an external signal. If the checking or the monitoring of the operation is necessary, it can be performed in a short time. Further, clogging can be detected when measurements of corpuscles are not being made.

Other objects and features of the invention will appear in the course of the description thereof which follows.

DETAILED DESCRIPTION OF THE PREFERRED EMBODIMENTS

Figure 1:
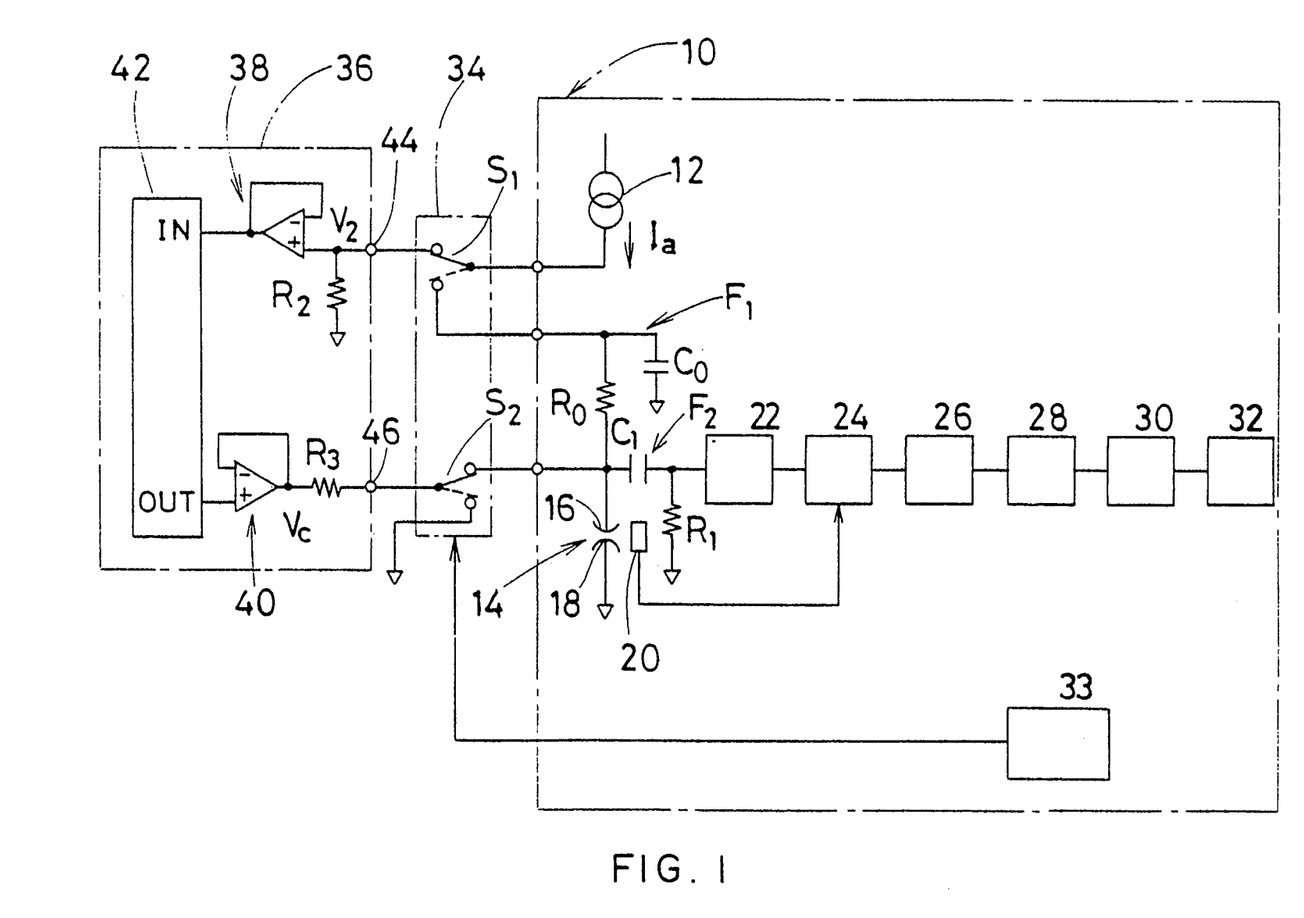
FIG. 1 is a circuit diagram of a corpuscle-detecting apparatus according to the invention.

Referring to FIG. 1, there is shown a corpuscle-detecting apparatus according to the invention. The body of the apparatus is generally indicated by reference numeral 10. The body 10 comprises a detector portion having an aperture 14 through which corpuscles pass, a pair of electrodes 16 and 18 disposed on opposite sides of the aperture 14, a constant-current source 12 (or a power supply) for supplying a constant current $I_a$ to the aperture 14 via the electrodes 16 and 18, a thermistor 20 acting as a liquid temperature sensor, amplifier circuits 22, 24, 26, a waveform-processing circuit 28, an A/D converter circuit 30, a data analysis portion 32, and a control portion 33. The detector portion produces an output signal (herein referred to as the corpuscle signal) in response to a change in the electrical impedance caused by the passage of corpuscles through the aperture 14.

The thermistor 20, the amplifier circuits 22, 24, 26, the waveform-processing circuit 28, the A/D converter circuit 30, and the data analysis portion 32 together form a corpuscle signal-processing means that processes the corpuscle signal produced from the detector portion.

The control portion 33 controls the various circuit units. In this example, the amplifier circuits 22, 24, and 26 are a preamplifier circuit, an amplifier circuit for compensating for liquid temperature variations, and an amplifier circuit for adjusting the gain, respectively.

The gain of the preamplifier circuit 22 is fixed. The liquid temperature-compensating amplifier circuit 24 varies the gain so that the sensitivity is regulated against variations in the liquid temperature. The gain-adjusting amplifier circuit 26 can vary the gain.

A resistor $R_0$ and a capacitor $C_0$ both of which are disposed between the constant-current source 12 and the aperture 14 together form a filter $F_1$ for removing noise from the current source 12. A resistor $R_1$ and a capacitor $C_1$ both of which are disposed between the aperture 14 and the preamplifier circuit 22 together form a filter $F_2$ for filtering out the DC component.

To count the number of corpuscles, adjustment of the sensitivity is first needed. The sensitivity adjustment is needed to absorb variations in characteristics among various components. The sensitivity is affected by the value of the current produced by the constant-current source 12, the inside diameter of the aperture 14 forming the detector portion, the path length in the aperture, and variations in the characteristics among the devices of the thermistor 20 and of the amplifier circuits 22, 24, and 26. To absorb these variations, it is necessary to adjust the sensitivity of the whole system including these components. Heretofore, any sensitivity adjustment method which can adjust the whole system including the measuring system by the use of a pseudo signal has not existed.

The present invention adds a pseudo signal-generating means 36 and a signal selector means 34 to the prior art corpuscle-detecting apparatus. The signal selector means 34 is switched between its first state and second state to switch the mode of operation between a pseudo signal mode and a normal measurement mode. The pseudo signal-generating means 36 produces a pseudo signal in the form of pulses. This pseudo signal has a peak value corresponding to the amplitude of the input current. When the pseudo signal is applied to the aperture, a resultant signal is equivalent to a corpuscle signal produced when corpuscles to be detected pass through the aperture 14. The signal selector means 34 is disposed between the pseudo signal-generating means 36 and the body 10 of the apparatus consisting of the aperture 14, the constant-current source 12, and the corpuscle signal-processing means. The signal selector means 34 is switched between its first state and second state. In the first state, the current from the current source 12 used for detection of corpuscles is supplied to the pseudo signal-generating means 36. The pseudo signal generated by the pseudo signal-generating means 36 is supplied to the aperture 14. In the second state, the current from the current source 12 used for detection of corpuscles is supplied to the aperture 14.

The circuit of FIG. 1 is described now. As an example, the signal selector means 34 consists of an externally operable relay. This selector means 34 is equipped with two switching means $S_1$ and $S_2$ which are an input switch and an output switch, respectively. These two switches are interlocked.

The pseudo signal-generating means 36 is now described in detail. This means 36 has an input terminal 44 with which a resistor $R_2$ for converting the input current into a voltage is connected. One end of the resistor $R_2$ is connected with the input terminal 44, while the other end is grounded. One end of the resistor $R_2$ is connected with a pulse signal-generating means 42 via a buffer circuit 38 having a high input impedance. That is, the voltage $V_2$ developed across the resistor $R_2$ is applied to the pulse signal-generating means 42 via the buffer circuit 38. The pulse signal-generating means 42 produces a pseudo signal $V_c$ at its output terminal 46 at a high output impedance via a buffer circuit 40 and a resistor $R_3$.

The apparatus further includes an external control means (not shown in FIG. 1) that controls the timing at which the pseudo signal $V_c$ is produced. The states of the switching means $S_1$ and $S_2$ of the signal selector means 34 consisting of the relay are switched to the other states simultaneously in response to an external control signal from the control portion 33. The signal selector means 34 assumes either a first state or a second state.

The first state is indicated by the solid lines in FIG. 1. The first state is the pseudo signal mode in which various adjustments, checks, monitoring, and other operations are performed. In this first state, the constant-current source 12 of the body 10 of the corpuscle-detecting apparatus is disconnected from the electrode 16 on one side of the aperture 14 and connected with the input terminal 44 of the pseudo signal-generating means 36. The output terminal 46 of the pseudo signal-generating means 36 is connected with the side of the aperture 14, or the electrode 16.

In the first state, the current $I_a$ from the constant-current source 12 used for detection of corpuscles is supplied to the pseudo signal-generating means 36 which detects the amplitude of the current $I_a$. Then, the pseudo signal-generating means 36 produces the pseudo signal $V_c$ having a peak value proportional to the amplitude of the current $I_a$. The pseudo signal $V_c$ which takes the form of pulses is supplied to one side of the aperture 14. As a result, a pseudo corpuscle signal is produced according to the circumstances of the detector portion such as the diameter of the aperture. The amplifier circuit 22 at the following stage etc. performs various kinds of processing such as amplification. Various adjustments, checks, and so forth can be performed according to the signal. When the sensitivity is adjusted, the gain of the amplifier circuit 26 is so adjusted that the peak value of the pseudo corpuscle signal induced by the above-described pseudo signal becomes a given value. When the operation is checked or monitored, the signal processed by the various circuits is checked or monitored according to the pseudo signal.

Clogging of the detector portion can be detected in advance by establishing the first state prior to measurements of corpuscles, producing the pseudo signal, and inspecting the sensitivity. Where the apparatus is designed so that it can modify the waveform or the amplitude of the pseudo signal $V_c$, the check performed by the following stage of signal-processing circuit (or the corpuscle signal-processing means) can be done with greater accuracy. These operations can be performed at any desired time, i.e., either prior to or after measurements of corpuscles.

The second state is indicated by the broken lines in FIG. 1. This second state is the normal measurement mode in which the corpuscle-detecting apparatus makes normal measurements of corpuscles. In this second state, the constant-current source 12 of the body 10 of the apparatus is disconnected from the pseudo signal-generating means 36 and connected with the electrode 16 on one side of the aperture 14 via the noise-removing filter $F_1$. The output terminal 46 of the pseudo signal-generating means 36 is disconnected from the electrode 16 on the side of the aperture 14 and grounded. In this second state, the body 10 of the apparatus makes normal measurements of corpuscles. The constant-current source 12 supplies the current $I_a$ used for detection of corpuscles to the aperture 14. Normal measurements of corpuscles are made. In the first state, the DC current $I_a$ supplied from the constant-current source 12 flows through the resistor $R_2$. A DC voltage given by $V_2 = R_2 \cdot I_2$ is set up across the resistor $R_2$. The value of the current $I_a$ is determined, taking account of various conditions, and according to the purpose. As an example, $I_2$ is 0.26 mA. $R_2 = 22$ k$\Omega$. Therefore, $V_2 = 5.72$ V.

The pulse signal-generating means 42 receives the voltage $V_2$ produced across the resistor $R_2$ for converting its input current into a voltage and produces successive pulses whose peak value is proportional to the voltage $V_2$. These pulses are produced as the pseudo signal $V_c$ at a high output impedance via the buffer circuit 40 and the resistor $R_3$, and are supplied to the aperture 14 from the electrode 16.

Figure 2:
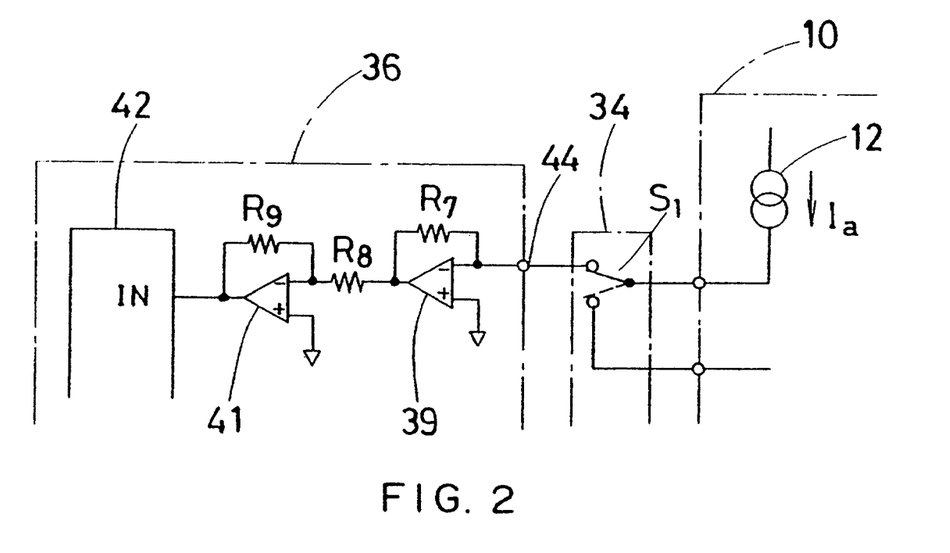
FIG. 2 is a circuit diagram of a pseudo signal-generating means different from the pseudo signal-generating means shown in FIG. 1.

FIG. 2 is a circuit diagram illustrating another example of the pseudo signal-generating means 36. FIG. 2 shows the input stage and its adjacent portion of the pseudo signal-generating means 36. Shown in this figure are a current-to-voltage converter circuit 39, an inverting amplifier circuit 41, and a pulse-generating means 42. A DC voltage given by $R_9 \cdot R_7 \cdot I_a / R_8$ is applied to the input IN of the pulse-generating means 42. The same voltage as obtained in FIG. 1 can be derived by appropriately selecting the values of resistors $R_7$, $R_8$ and $R_9$.

Figure 3:
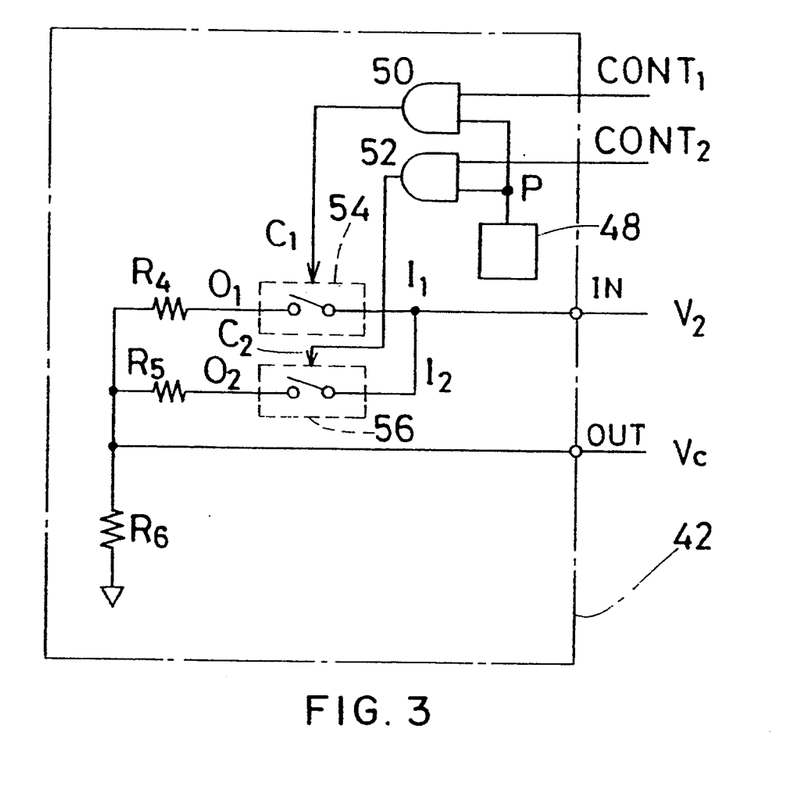
FIG. 3 is a circuit diagram of the pulse signal-generating generating means shown in FIG. 1.
Figure 4:
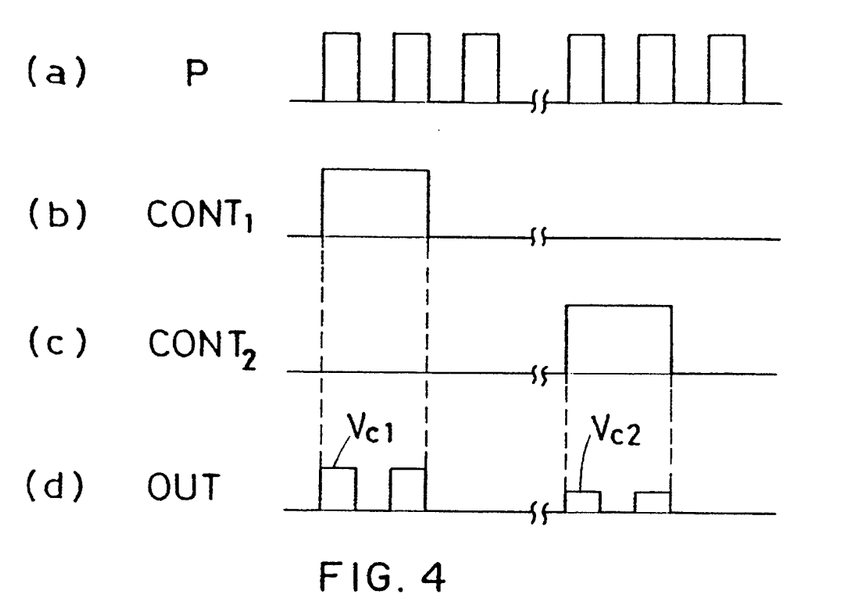
FIG. 4 is a timing chart illustrating the operation of the pulse signal-generating means shown in FIG. 3.

FIG. 3 is a circuit diagram of a specific example of the pulse signal-generating means 42. FIG. 4 is a timing chart showing various signals produced at various portions of the circuit of FIG. 3.

Referring to FIG. 3, an oscillator 48 produces a pulse signal P from which a pseudo signal is created. As an example, the pulse width of this pulse signal is 12.5 $\mu$s, and the pulse interval is 1.5 ms. Preferably, the pseudo signal approximates a corpuscle signal obtained when corpuscles are actually measured. Although the optimum pseudo signal is sine square wave, the configuration for producing the signal is complex.

On the other hand, it is easy to produce a rectangular wave. Experiment has shogun that a rectangular wave yields satisfactory results. An example in which a rectangular wave is used as the pseudo signal is described next. The characteristics of the following stage of circuit are so set that it removes RF components. Therefore, the RF components of the rectangular wave are filtered out. This permits the use of a rectangular wave.

The output of the oscillator 48 is connected with one input of an AND circuit 50 and with one input of another AND circuit 52. External control signals $CONT_1$ and $CONT_2$ are applied to the other inputs of the AND circuits 50 and 52, respectively. The DC voltage $V_2$ developed across, the resistor $R_2$ is applied to one end $I_1$ of an analog switch 54 and also to one end $I_2$ of another analog switch 56. These alalog switches 54 and 56 have control terminals $C_1$ and $C_2$, respectively, to which the pulse signals from the AND circuits 50 and 52 are applied, thus opening and closing the switches 54 and 56. Pulse signals whose peak values are equal to the voltage $V_2$ appear at the other ends $O_1$ and $O_2$, respectively. Resistors $R_4$, $R_5$ and $R_6$ are used for adjustments of the peak values.

As shown in FIG. 4, $(a)$–$(d)$, when the external signal $CONT_1$ is at high level and the external signal $CONT_2$ is at low level, i.e., when the analog switch 54 is closed, the pulse signal P of the peak value $V_2$ is divided by the resistors $R_4$ and $R_6$, so that plural pulses $V_{c1}$ having a peak value of $V_2 \cdot R_6/(R_4+R_6)$ is produced as a pseudo signal from the output OUT at regular intervals of time.

Conversely, when the external signal $CONT_1$ is at a low level and the external signal $CONT_2$ is at high level, i.e., when the analog switch 56 is closed, the pulse signal P is divided by the resistors $R_5$ and $R_6$, whereby plural pulses $V_{c2}$ having a peak value of $V_2 \cdot R_6/(R_5+R_6)$ is produced as a pseudo signal from the output OUT at regular intervals of time.

In this way, pseudo signals having different peak values can be obtained selectively. Each pseudo signal is a pulse signal having a peak value proportional to the current $I_a$ used for detection of corpuscles. For example, one pseudo signal can be used for detection of red blood cells, while the other can be employed for detection of blood platelets.

It is also possible to provide two oscillators each of which is equivalent to the oscillator 48. These two oscillators are connected with the AND circuits 50 and 52, respectively. Thus, pseudo signals having different pulse widths and different pulse spacings can be produced. The operation can be inspected with greater accuracy by producing plural kinds of pseudo signals in this way. The circuit of FIG. 1 is next analyzed in great detail.

(1) When the signal selector means 34 assumes the second state, i.e., when the normal measurement mode has been established.

Figure 5:
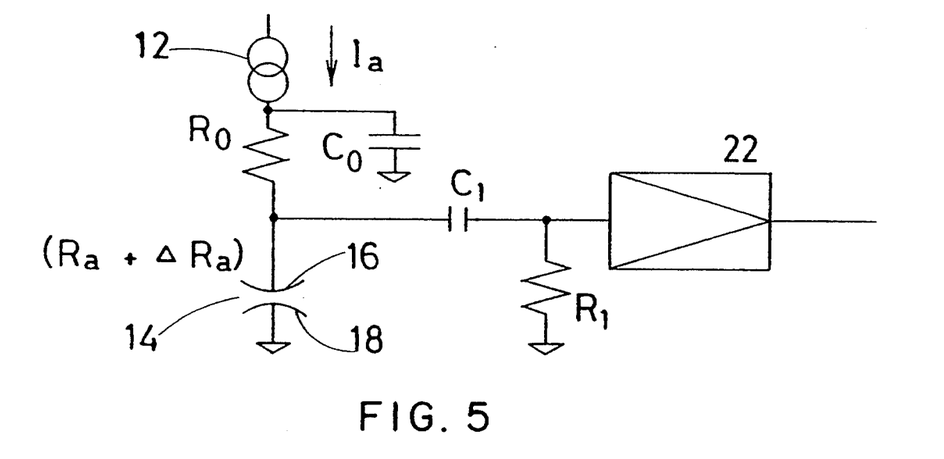
FIG. 5 is a circuit diagram of the aperture and its adjacent portion of the corpuscle-detecting apparatus shown in FIG. 1.

FIG. 5 is a circuit diagram of the detector portion and its adjacent portion, i.e., the aperture and its surroundings, of the corpuscle-detecting apparatus shown in FIG. 1, and in which the apparatus is operating in the normal measurement mode. Let $R_a$ be the electrical resistance of the aperture 14 when no corpuscle exists in the aperture 14 and only diluting liquid passes through the aperture. Let $(R_a + \Delta R_a)$ be the electrical resistance of the aperture when corpuscles passed through it. The change $\Delta R_a$ in the electrical resistance is in proportion to the volume V of the corpuscles to be investigated.

Figure 6:
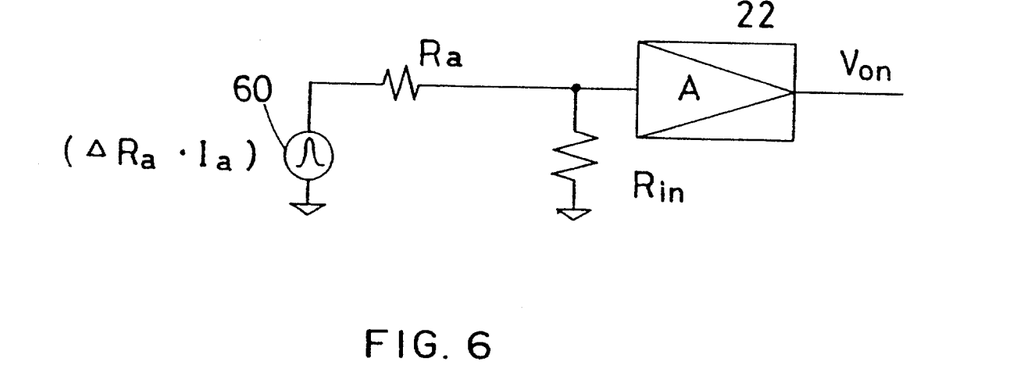
FIG. 6 is an equivalent circuit diagram of the circuit of FIG. 5, and in which only alternating current is taken into consideration.

FIG. 6 is an equivalent circuit diagram of the circuit of FIG. 5 when only alternating current is taken into account. Indicated by 60 is an equivalent AC power supply induced by the change $\Delta R_a$ in the electrical resistance. $R_{in}(=R_0 \cdot R_1/(R_0+R_1))$ represents a parallel combination of resistors $R_0$ and $R_1$. A represents the gain of the amplifier circuit 22. The peak value of the output $V_{on}$ can be given by $$V_{on} = \Delta R_a \cdot I_a \cdot \{R_{in}/(R_a+R_{in})\} \cdot A \tag{1}$$

(2) When the signal selector means 34 assumes the first state, i.e., when the pseudo signal mode has been established.

Figure 7:
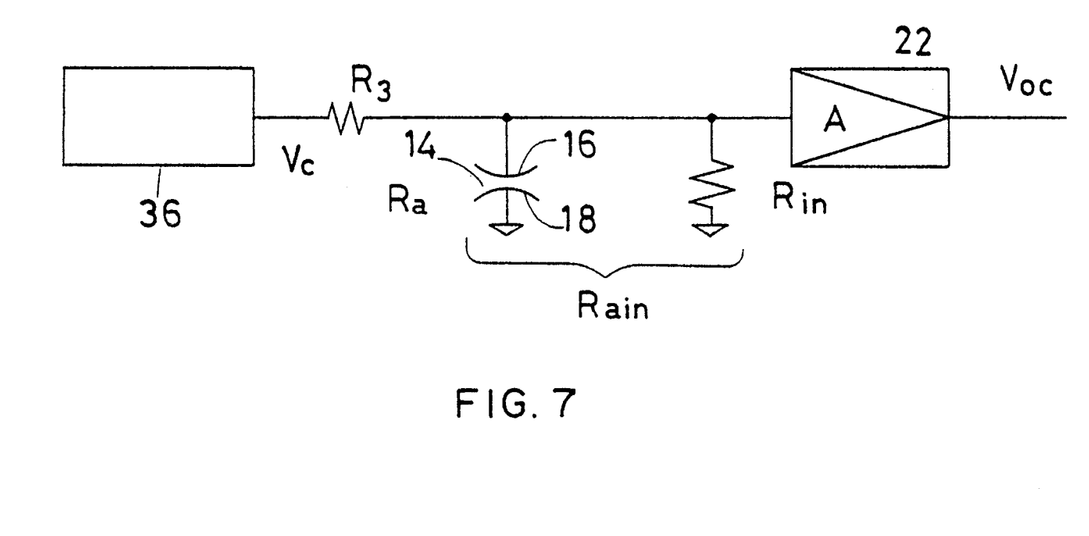
FIG. 7 is an equivalent circuit diagram of the aperture and its adjacent portion of the corpuscle-detecting apparatus shown in FIG. 1, and in which the apparatus is operating in the pseudo signal mode.

FIG. 7 is a circuit diagram of the detector portion and its adjacent portion, i.e., the aperture and its surroundings, in the pseudo signal mode. Let $V_c$ be the output signal from the pseudo signal-generating means 36. The output $V_{oc}$ from the amplifier circuit 22 can be given by $$V_{oc} = V_c \cdot \{R_{ain}/(R_{ain}+R_3)\} \cdot A \tag{2}$$

where $R_{ain}$ indicates a parallel combination of the resistors $R_a$ and $R_{in}$. We have $$R_{ain} = R_a \cdot R_{in}/(R_a+R_{in}) \tag{3}$$

Substitution of equation (3) into equation (2) results in $$V_{oc} = V_C \cdot R_a/R_3 \cdot [R_{in}/\{R_a(1+R_{in}/R_3)+R_{in}\}] \cdot A \tag{4}$$

If the value of the resistor $R_3$ is so selected that the relation $R_3 >> R_{in}$ holds, then we have $$V_{oc} = V_c/R_3 \cdot R_a \cdot \{R_{in}/(R_a+R_{in}) \cdot A\} \tag{5}$$

From equations (1) and (5), we have $$V_{oc} = \{(V_c/I_a)/R_3 \cdot (R_a/\Delta R_a)\} \cdot V_{on} \tag{6}$$

In the present invention, the pseudo signal $V_c$ is made to be in proportion to the current $I_a$ used for detection of corpuscle, i.e., $$V_c = K_3 \cdot I_a \tag{7}$$

It is known that $$\Delta R_a = k_1 \cdot \rho(t) \cdot v/D^4 \tag{8}$$

$$R_a = k_2 \cdot \rho(t) \cdot L/D^2 \tag{9}$$

where $k_1$ and $k_2$ are constants, v is the volume of the control corpuscles and constant, $\rho(t)$ is the resistivity of suspension of corpuscles at temperature t, D is the diameter of the aperture, and L is the path length in the aperture. Therefore, equation (6) can be changed into $$V_{oc} = K \cdot (L \cdot D^2) \cdot V_{on} \tag{10}$$

It is to be noted that $K = (K_3/R_3) \cdot (k_2/k_1)/v$. That is, the signal voltage $V_{oc}$ is correlated with the signal voltage $V_{oc}$ with a constant $K \cdot (L \cdot D^2)$ which depends on the dimensions of the aperture. K is independent of the liquid temperature. The coefficient $K_3$ included in the above equation is a constant determined by the resistances $R_2$, $R_4$ (or $R_3$), and $R_6$.

It is now assumed that the dimensions of the aperture do not vary among apparatuses. By appropriately selecting the values of the resistances $R_2$, $R_4$ (or $R_5$), and $R_6$, the following relationship can be obtained:

$$V_{oc} = V_{on}$$

This means that the corpuscle signal obtained by a measurement using a control corpuscle is equivalent to the corpuscle signal obtained by the use of a pseudo signal, and that the sensitivity can be adjusted with a pseudo signal without using any control corpuscle. Thus, the adjustment of the sensitivity is carried out by adjusting the gain of the amplifier circuit 26 in such a way that an item (e.g., the mean corpuscular volume) regarding the size of a corpuscle assumes a given value.

In practice, however, the equation (10) includes the item $(L \cdot D^2)$ which depends on the dimensions of the aperture, it being noted that the dimensions of the aperture vary from apparatus to apparatus. Also, the assumption $R_3 >> R_{in}$ involves error. These variations and error cause the result of the sensitivity adjustment to vary among apparatuses.

$R_3 >> R_{in}$ means that the output impedance of the pseudo signal-generating means 36 is high. Therefore, where the corpuscle-detecting apparatus shown in FIG. 1 is equipped with the pseudo signal-generating means 36, it is necessary that the output impedance of the pseudo signal-generating means 36 be high.

In this example, the values of the resistors $R_3$, $R_0$, and $R_1$ are set to 560 k$\Omega$, 740 k$\Omega$, and 1 M$\Omega$, respectively. Since the resistance $R_{in}$ is a parallel combination of the resistors $R_0$ and $R_1$, it is 68.9 k$\Omega$. Note that if the resistance $R_{in}$ is too small, then the sensitivity is deteriorated. If the resistance $R_3$ is too large, leakage of signal tends to occur.

Figure 8:
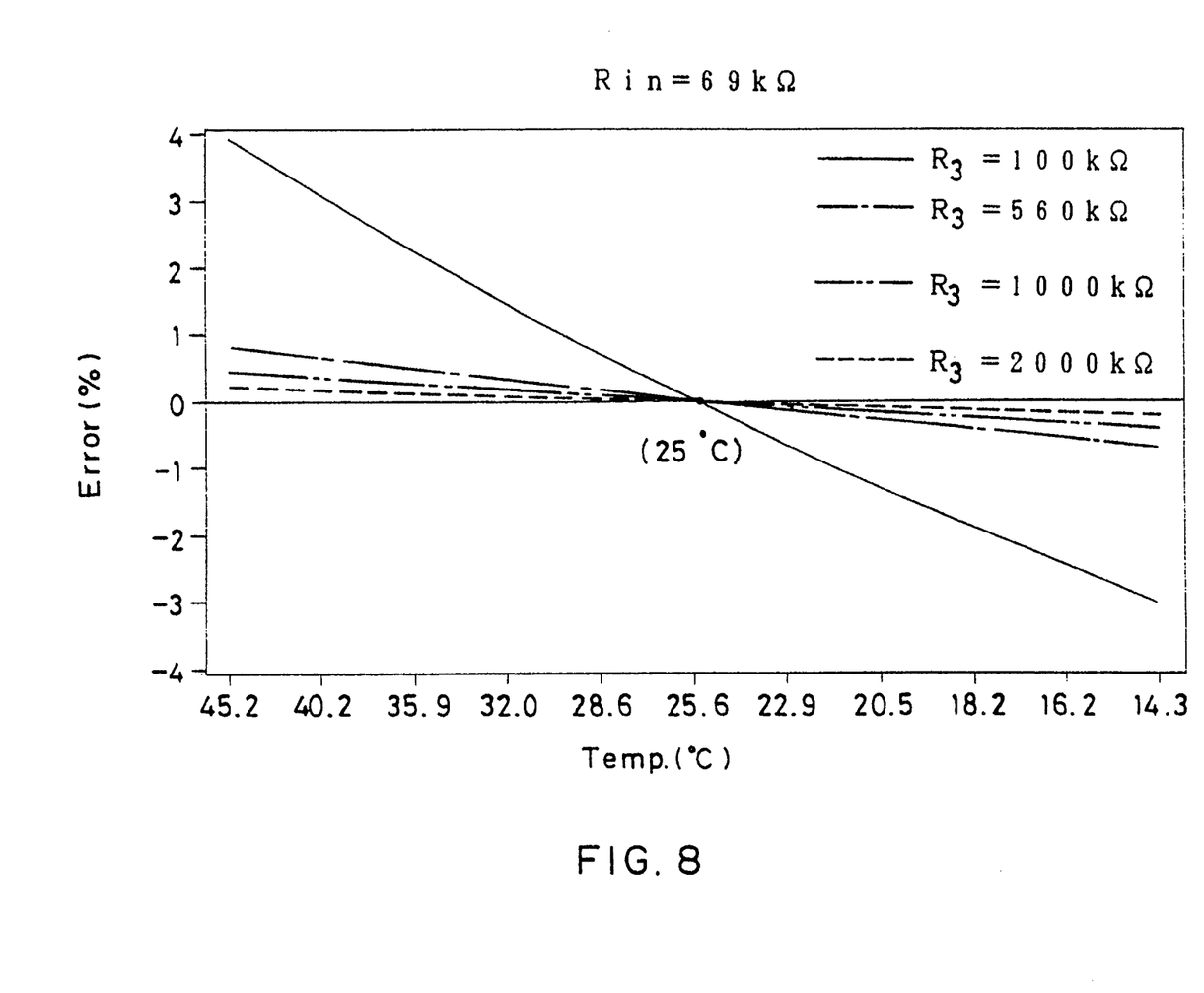
FIG. 8 is a graph illustrating the relation of the amount of error to the temperature of liquid sample.

FIG. 8 is a graph showing the relation of the error caused by the assumption $R_3 >> R_{in}$ to the liquid temperature, for illustrating the error. This graph shows the error induced in the result of the adjustment of the sensitivity when the liquid temperature is varied. The resistance $R_{in}$ is 68.9 k$\Omega$ ($\approx$69 k$\Omega$). The resistance $R_3$ is 560 k$\Omega$. The error is within $\pm 1\%$ when the liquid temperature lies within the range from 15° C. to 35° C. Of course, the error increases with reduction the resistance $R_3$.

In FIG. 8, the characteristic obtained when the resistance $R_3$ is 560 k$\Omega$ is indicated by the dot-and-dash line. The characteristic obtained when the resistance $R_3$ is 100 K$\Omega$ is indicated by the solid line. The characteristic obtained when the resistance $R_3$ is 1000 K$\Omega$ is indicated by the phantom line. The characteristic obtained when the resistance $R_3$ is 2000 K$\Omega$ is indicated by the broken line.

The error induced in the adjustment of the sensitivity by the dimensions of the aperture can be reduced by measuring the dimensions in advance and adjusting the sensitivity of each individual apparatus, taking account of the dimensions.

In the present invention, the peak value of the pseudo signal $V_c$ is in proportion to the value of the current $I_a$ from the constant-current source 12 used for detection of corpuscles and so the adjustment of the sensitivity is not affected by variations in the current $I_a$ among apparatuses. We changed the value of the current $I_a$ in such way that it deviated $+10\%$ from the reference value. However, we observed that the current change caused no error in the adjustment of the sensitivity.

In this way, the sensitivity can be adjusted without using control corpuscle, though a slight amount of error exists. The adjustment is not affected by variations in the electrical system such as variations in the detected current and variations in the constants of the amplifier circuits. Finally, the sensitivity is confirmed, using control corpuscles. However, the adjustment of the sensitivity is completed at the previous stage and, therefore, only a fine adjustment using control corpuscles is needed subsequently. Hence, the amount of control corpuscles consumed and the time required for the sensitivity adjustment can be reduced greatly.

Furthermore, clogging of the aperture 14 can be found in advance by checking the amplitude of the pseudo corpuscle signal in the pseudo signal mode prior to normal measurement. If the aperture is clogged, the resistance $R_a$ increases. As can be seen from equation (5), the signal $V_{oc}$ increases. The clogging can be found by detecting this increase in the signal.

Additionally, it is possible to know whether the various circuits of the corpuscle-detecting apparatus are operating normally or not by checking the size distribution obtained from the pseudo signal.

In a corpuscle-detecting apparatus, a pressure difference is created between the opposite sides of the aperture. The liquid on one side is forced through the aperture and moved to the other side. Normally, a liquid is put into the detection chamber. The liquid is drawn through the aperture. First, a cleaning liquid is injected into the detection chamber to clean the inside of the chamber. Then, the cleaning liquid is completely discharged. Subsequently, the liquid sample or blood cell suspension to be investigated is put into the chamber. If the liquid sample enters while the cleaning liquid remains in the detection chamber, then it is possible to make a correct measurement. Accordingly, a pseudo signal is produced just when the cleaning liquid is discharged. Thus, the presence or absence of a liquid inside the chamber can be detected. That is, the impedance of the aperture varies, depending on whether a liquid is present in the chamber or not. Therefore, a signal obtained by the use of a pseudo signal has different amplitudes. This difference is detected. As a result, it is possible to know whether the liquid has been discharged or not.

Figure 9:
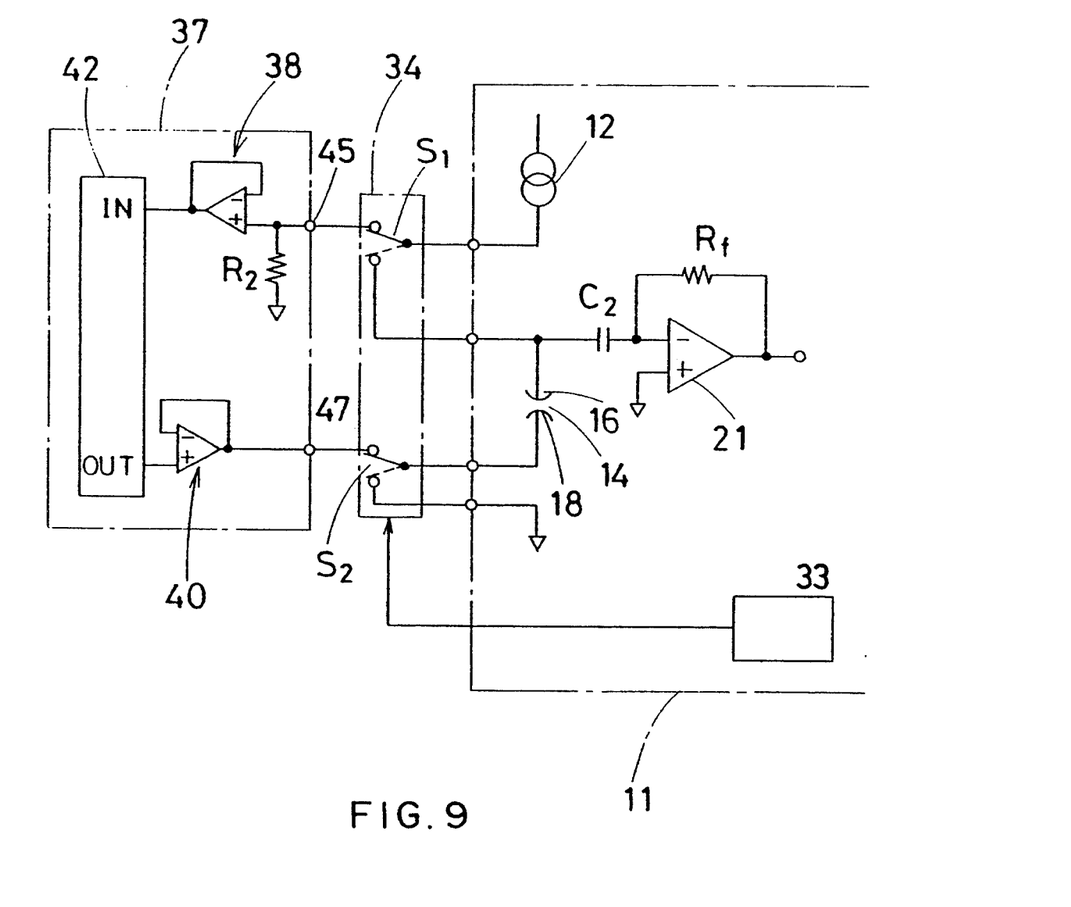
FIG. 9 is a circuit diagram of main portions of another corpuscle-detecting apparatus according to the invention.

Referring next to FIG. 9, there is shown a corpuscle-detecting apparatus different from the apparatus shown in FIG. 1. The body, indicated by numeral 11, of this apparatus is equipped with a pseudo signal-generating means according to the invention. Since the body 11 of the apparatus is known, it is not described in detail below. A signal selector means 34 has an input switching means $S_1$ and an output switching means $S_2$ in the same way as the signal selector means 34 shown in FIG. 1. However, the switching means $S_2$ is connected in a manner different from the switching means $S_2$ shown in FIG. 1. An operational amplifier 21, a capacitor $C_2$, and a resistor $R_f$ together form a current-to-voltage converter circuit which converts the current variation produced in the aperture 14 into a voltage change. A pseudo signal-generating means 37 is similar to the pseudo signal-generating means 36 shown in FIG. 1 except that the resistor $R_3$ is omitted.

When the signal selector means 34 takes its first state, i.e., the apparatus is operating in the pseudo signal mode as indicated by the solid lines, a constant-current source 12 is disconnected from the side of the aperture 14 by the switching means $S_1$ and connected with the input terminal 45 of the pseudo signal-generating means 37. The output terminal 47 of the pseudo signal-generating means 37 is connected with an electrode 18 on one side of the aperture 14 by the switching means $S_2$.

When the signal selector means 34 assumes its second state, i.e., the apparatus is operating in the normal measurement mode as indicated by the broken lines, the constant-current source 12 is disconnected from the pseudo signal-generating means 37 by the switching means $S_1$ and connected with an electrode 16 on the other side of the aperture 14. The other electrode 18 on the side of the aperture 14 is grounded by the switching means $S_2$.

The same concept applies in examining the circuit of FIG. 9 as described in connection with FIG. 1. Therefore, only the results are given below. Signal voltages $V_{on}$ and $V_{oc}$ are respectively given by $$V_{on} = (\Delta R_a/R_a) \cdot I_a \cdot R_f \quad (11)$$

$$V_{oc} = -(R_f/R_a) \cdot V_c \quad (12)$$

Therefore, equation (12) can be changed into the form $$V_{oc} = K_3/\Delta R_a \cdot V_{on} = K_4 \cdot D^4/p(t) \cdot V_{on} \quad (13)$$

where $K_4 = K_3/k_1/v$.

The signal voltage $V_{oc}$ is correlated with the signal voltage $V_{on}$ with a constant $K_4 \cdot D^4/p(t)$. In consequence the sensitivity adjustment produces error due to the liquid temperature t and due to the dimensions of the aperture $D^4$. However, the sensitivity adjustment using pseudo signals is made sufficiently useful by taking account of these variations in the same way as in the apparatus described in conjunction with FIG. 1 though the adjustment is not perfect.

In the embodiments described thus far, the signal selector means 34 is equipped with the two switching means and $S_2$. In the description made below, only one switching $S_1$ means is provided.

Figure 10:
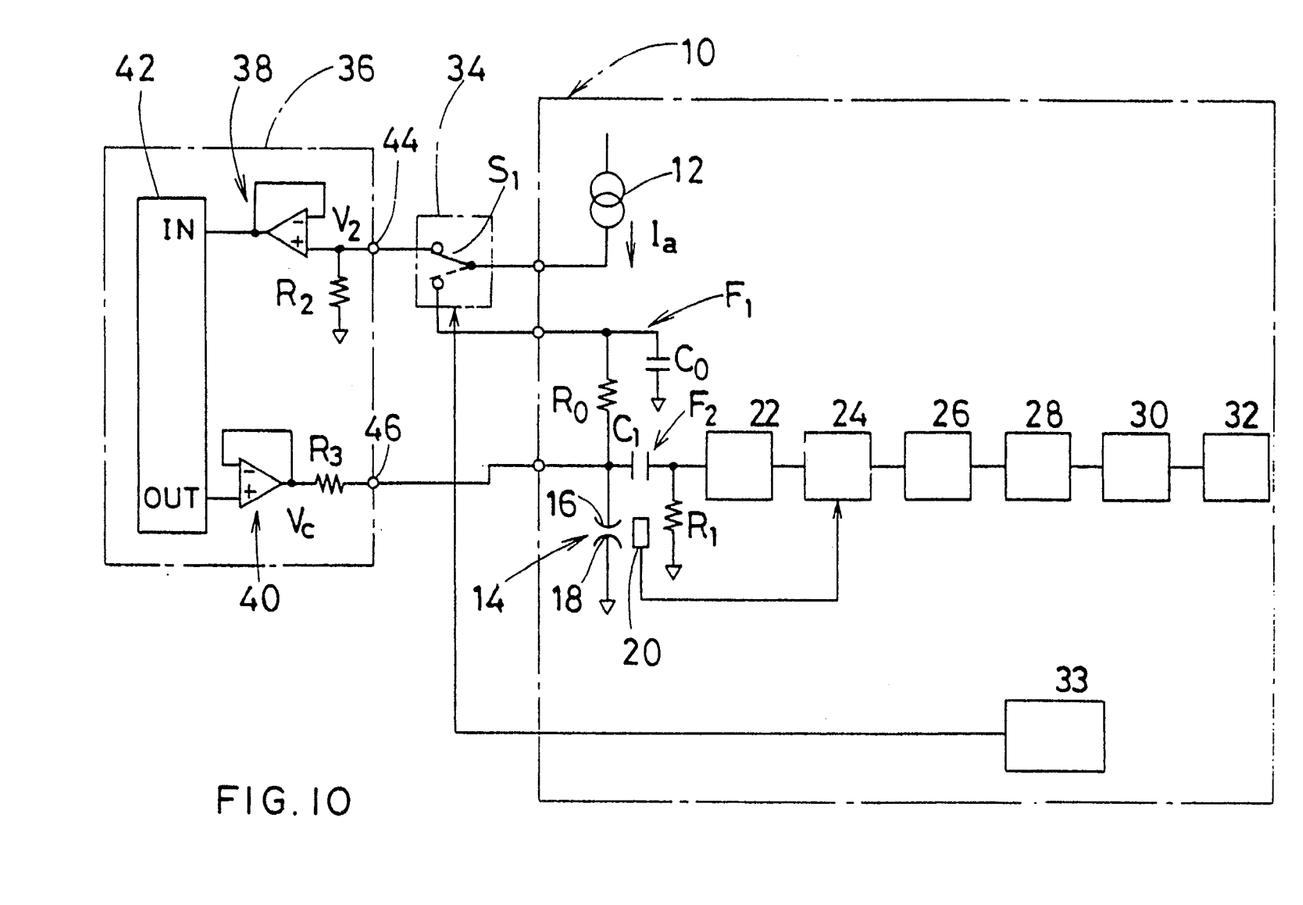
FIG. 10 is a circuit diagram of a further corpuscle-detecting apparatus according to the invention.
Figure 11:
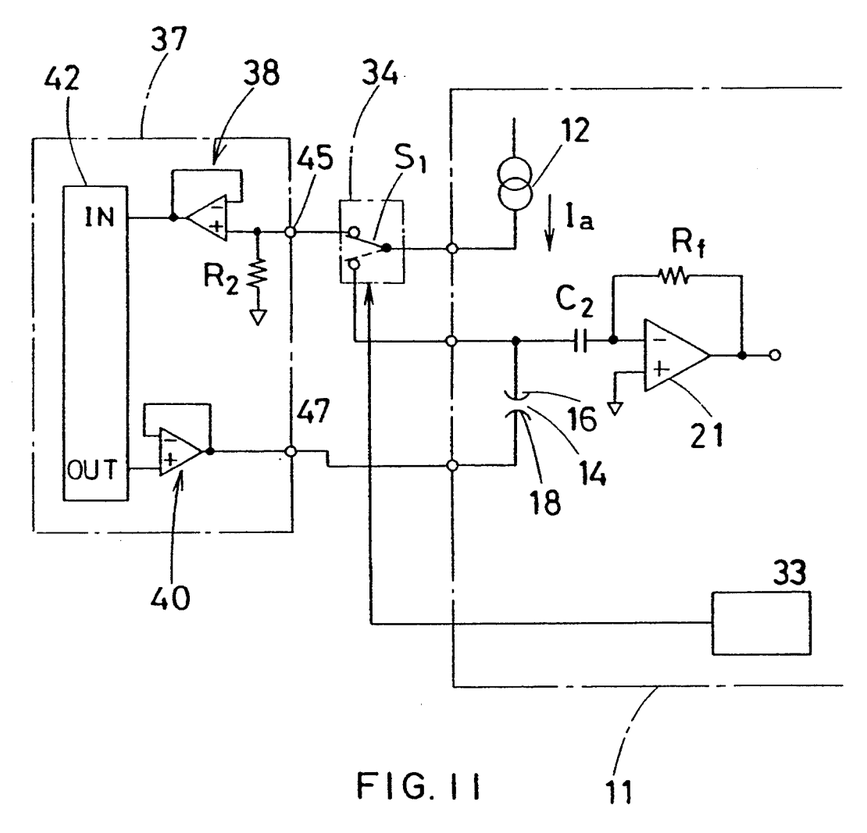
FIG. 11 is a circuit diagram of main portions of a still other corpuscle-detecting apparatus according to the invention.

FIGS. 10 and 11 correspond to FIGS. 1 and 9, respectively. In the configurations shown in FIGS. 10 and 11, only one input switching means $S_1$ is provided, and the output of the pseudo signal means 37 is kept directly connected with the side of the aperture. In the first state, or the pseudo signal mode, FIGS. 10 and 11 are the same as FIGS. 1 and 9, respectively. In the second state, or in the normal measurement mode, FIGS. 10 and 11 assume states different from those of FIGS. 1 and 9 as described below.

In the corpuscle-detecting apparatus shown in FIG. 10, the constant-current source 12 is not connected with the pseudo signal-generating means 36. Therefore, the output of the buffer circuit 40 can be regarded as being at 0 V, or ground level. Where $R_3 >> R_{in}$, the electrode 16 on the side of the aperture 14 is grounded via a large resistance $R_3$. Consequently, the effect of the permanent connection of the output of the pseudo signal-generating means 36 with the side of the aperture 14 is very small. Hence, the configuration of FIG. 10 yields substantially the same advantages as the configuration of FIG. 1.

In FIG. 10, if a capacitor C is connected in series with the resistor $R_3$ in the output portion, then the effect of the connection of the pseudo signal-generating means 36 is eliminated provided that only direct current is treated. Consequently, the configuration of FIG. 10 yields the same advantages as the configuration of FIG. 1. In this case, the liquid temperature produces totally no effect irrespective of the value of the resistor $R_3$. However, if the resistance $R_3$ is made too small, then the sensitivity with which the apparatus detects corpuscles is deteriorated.

In FIG. 11, the output of the buffer circuit 40 can be similarly regarded as being at 0 V, or at ground level. This is equivalent to the circuit of FIG. 9 in which the switching means $S_2$ is grounded. Consequently, the configuration of FIG. 11 yields the same advantages as the configuration of FIG. 9.

What is claimed is:

1. A corpuscle-detecting apparatus comprising:
    a detector portion having an aperture through which corpuscles to be investigated pass, the detector portion acting to produce a signal in response to a change in the electrical impedance that is caused by passage of the corpuscles through the aperture;
    a power supply which supplies an electrical current to the aperture for detection of the corpuscles;
    a corpuscle signal-processing means which processes the output signal from the detector portion;
    a pseudo signal generating means for producing a pseudo signal comprising pulses, said pseudo signal having a peak value corresponding to an amplitude of the electrical current of said power supply;
    a signal selector means mounted between (i) the pseudo signal-generating means and (ii) the aperture, the power supply, and the corpuscle signal-processing means, the signal selector means being switched between (i) a first state in which the electrical current from the power supply is supplied to the pseudo signal-generating means and the pseudo signal produced by the pseudo signal-generating means is supplied to the aperture wherein a signal produced by said detector portion in accordance with said pseudo signal is equivalent to the signal produced in response to passage of corpuscles through the aperture and (ii) a second state in which the electrical current from the power supply is supplied to the aperture.

2. The corpuscle-detecting apparatus of claim 1, wherein
    (A) said signal selector means has a first and a second switching means respectively connected to an input and an output of the pseudo signal-generating means;
    (B) when the signal selector means assumes said first state, the first switching means disconnects the power supply from an electrode on one side of the aperture and connects the power supply with the input of the pseudo signal-generating means, and the second switching means connects the output of the pseudo signal-generating means with said electrode; and
    (C) when the signal selector means assumes its second state, the first switching means disconnects the power supply from the input of the pseudo signal-generating means and connects the power supply with said electrode, and the second switching means disconnects the output of the pseudo signal-generating means from the electrode on the side of the aperture.

3. The corpuscle-detecting apparatus of claim 1, wherein
    (A) the output of the pseudo signal-generating means is directly connected with an electrode on one side of the aperture;
    (B) the signal selector means has a switching means connected with the input of the pseudo signal generating means;
    (C) when the signal selector means assumes said first state, the switching means disconnects the power supply from said electrode and connects the power supply with the input of the pseudo signal-generating means; and
    (D) when the signal selector means assumes its second state, the switching means disconnects the power supply from the input of the pseudo signal-generating means and connects the power supply with said electrode.

4. The corpuscle-detecting apparatus of claim 1, wherein said pseudo signal-generating means has a control means that externally controls the timing at which the pseudo signal is produced.

5. The corpuscle-detecting apparatus of claim 1, wherein said pseudo signal-generating means comprises a current-to-voltage converting resistor for receiving the current from the power supply and a pulse signal-generating means for producing plural pulses at regular intervals of time, the pulses having a peak value proportional to the voltage developed across the current-to-voltage converting resistor, and wherein the pulses are delivered as said pseudo signal.

6. The corpuscle-detecting apparatus of claim 5, wherein said pulse signal-generating means comprises: an analog switch having one end to which the voltage developed across said current to voltage converting resistor is applied; an oscillator producing pulses at regular intervals of time to control the analog switch; and a pulse signal supply means for supplying the pulses for controlling the analog switch to the control terminal of the analog switch during a desired period, the other end producing pulses having a peak value proportional to the voltage developed across the resistor.

7. The corpuscle-detecting apparatus of claim 1, wherein said pseudo signal-generating means comprises:
   first means for generating said pulses; and
   second means for receiving an external control signal and for controlling said first means to generate said pulses to have a predetermined pulse width in response to said external control signal.

8. The corpuscle-detecting apparatus of claim 1, wherein said pseudo signal-generating means comprises
   first means for generating said pulses; and
   second means for receiving an external control signal and for controlling said first means to generate said pulses to have a predetermined pulse interval in response to said external control signal.

* * * * *